United States Patent [19]

Okita

[11] 4,208,745

[45] * Jun. 24, 1980

[54] VASCULAR PROSTHESES COMPOSED OF POLYTETRAFLUOROETHYLENE AND PROCESS FOR THEIR PRODUCTION

[75] Inventor: Koichi Okita, Osaka, Japan

[73] Assignee: Sumitomo Electric Industries, Ltd., Osaka, Japan

[*] Notice: The portion of the term of this patent subsequent to Apr. 4, 1995, has been disclaimed.

[21] Appl. No.: 821,859

[22] Filed: Aug. 4, 1977

Related U.S. Application Data

[63] Continuation-in-part of Ser. No. 760,789, Jan. 19, 1977, abandoned.

[30] Foreign Application Priority Data

Jan. 21, 1976 [JP] Japan .................................. 51-6200

[51] Int. Cl.² .......................... A61F 1/24; B29C 17/02
[52] U.S. Cl. ............................................... 3/1.4; 3/1; 128/DIG. 14; 264/288.8; 264/289.3; 264/290.2; 428/376

[58] Field of Search ................ 3/1.4, 1; 128/DIG. 14; 264/288.8, 289.3, 290.2; 428/376

[56] References Cited

U.S. PATENT DOCUMENTS

| | | | |
|---|---|---|---|
| 3,094,762 | 6/1963 | Jeckel | 3/1.4 X |
| 3,473,087 | 10/1969 | Slade | 252/511 X |
| 3,953,566 | 4/1976 | Gore | 264/288 |
| 4,061,134 | 12/1977 | Samuels et al. | 3/1.4 X |
| 4,082,893 | 4/1978 | Okita | 428/376 |

FOREIGN PATENT DOCUMENTS 2508570  10/1975  Fed. Rep. of Germany ............... 3/1.4

Primary Examiner—Richard D. Lovering
Attorney, Agent, or Firm—Sughrue, Rothwell, Mion, Zinn and Macpeak

[57] ABSTRACT

A vascular prosthesis comprising a tubing of porous polytetrafluoroethylene, the polytetrafluoroethylene tubing having a fibrous structure of nodes and fibers connecting the nodes together and having a structure in which the fibrous structure at the inside surface of the tubing is finer than the fibrous structure at the outside surface of the tubing.

19 Claims, 5 Drawing Figures

VASCULAR PROSTHESES COMPOSED OF POLYTETRAFLUOROETHYLENE AND PROCESS FOR THEIR PRODUCTION

CROSS REFERENCE TO RELATED APPLICATIONS

This application is a continuation-in-part of co-pending application Ser. No. 760,789, VASCULAR PROSTHESES COMPOSED OF POLYTETRAFLUOROETHYLENE, filed Jan. 19, 1977, by Koichi Okita now abandoned.

BACKGROUND OF THE INVENTION

1. Field of the Invention

This invention relates to an artificial blood vessel composed of polytetrafluoroethylene, and more specifically, to a vascular prosthesis of a tubular fibrous construction whose inner surface consists of finer fibers than its outer surface, which is expected to expedite the healing of the anastomoses and development of the neointima after a surgical implant operation.

2. Description of the Prior Art

Fabric prostheses composed of a knitted or woven fabric of Dacron or polytetrafluoroethylene having inner diameters that are relatively large are now being utilized, with relatively good results. In particular, good results are generally obtained with vascular prostheses for arteries which have an inner diameter of at least about 7 mm. Despite this, few small inner diameter arteries are clinically acceptable. In venous applications, small inner diameter prostheses show a lower patency rate than in arterial application. The rate of blood flow in veins is smaller than in arteries, and to prevent thrombosis, it is important to inhibit platelet adhesion to the inner surface of the artificial veins. This requirement is not fully met by presently available artificial veins.

Some tubings made of stretched or expanded polytetrafluoroethylene have been demonstrated to be clinically useful as vascular prostheses for arteries and veins. This is described, for example, in Soyer et al., "A New Venous Prosthesis", *Surgery*, Vol. 72, pages 864 (1972), Volder et al., "A-V Shunts Created in New Ways", *Trans. Amer. Soc. Artif. Int. Organs*, Vol. 19, p. 38 (1973), Matsumoto et al., "A New Vascular Prosthesis for a Small Caliber Artery", *Surgery*, Vol. 74, p. 519 (1973), "Application of Expanded Polytetrafluoroethylene to Artificial Vessels", *Artificial Organs*, Vol. 1, p. 44 (1972), Ibid., Vol. 2, p. 262 (1973), and Ibid., Vol. 3, p. 337 (1974), Fujiwara et al., "Use of Goretex Grafts for Replacement of the Superior and Inferior Venae Canal", *The Journal of Thoracic and Cardiovascular Surgery*, Vol. 67, p. 774 (1974), and Goldfarb, Belgian Pat. No. 517,415.

The results of these clinical experiments are summarized below.

When a suitable porous prosthesis is implanted as a conduit within the arterial system, the fine pores are clogged by clotted blood, and the inside of the prosthesis is covered with the clotted blood layer. The clotted blood layer is made up of fibrin, and its thickness varies according, for example, to the material of the prosthesis, and the surface structure of the prosthesis. Since the thickness of fibrin approaches 0.5 to 1 mm when a knitted or woven fabric of Dacron or polytetrafluoroethylene is used as the prosthesis, success is achieved only with those blood vessels which are not occluded by this increase in the wall thickness by the fibrin layer (that is, arteries having an inside diameter of 5 to 6 mm or more). Generally, knitted or woven prosthesis having smaller inner diameters have not been successful.

A polytetrafluoroethylene tubing which has been stretched has a microstructure composed of very fine fibers and nodes connected together by the fibers. The diameters of the fibers vary depending on various stretching conditions, and can be made much smaller than fibers of the knitted and woven fabrics mentioned above.

It has been confirmed clinically that when a structure composed of fibers and nodes is expressed in terms of pore sizes and porosities, or fiber lengths and nodular sizes, a polytetrafluoroethylene tubing having a pore size of from about $2\mu$ to about $30\mu$ (pore sizes below about $2\mu$ are undesirable), a porosity of about 78% to about 92%, a fiber length of not more than about $34\mu$ (fiber lengths of about $40\mu$ to about $110\mu$ are undesirable), a nodular size of not more than about $20\mu$, and a wall thickness of about 0.3 mm to about 1 mm exhibits a high patency rate without substantial occlusion by fibrin deposition.

It has been reported, however, that venous prosthesis shows a much lower patency rate than arterial prosthesis, and does not prove to be entirely satisfactory for prosthetic purposes. It has also been reported that when the vascular prosthesis has too high a porosity, a tearing of the prosthesis by the suture used in joining the prosthesis with the vessel of the patient tends to occur.

SUMMARY OF THE INVENTION

A primary object of this invention, therefore, is to provide a vascular prosthesis of a stretched polytetrafluoroethylene tubing in which the fibrous structure at the inside surface is made of finer fibers than the fibrous structure at the outside surface.

Another object of this invention is to provide a vascular prosthesis of a stretched polytetrafluoroethylene tubing in which the fibers on the outside surface have a diameter at least two times larger than the fibers on the inside surface so as to prevent a tearing of the tubing in the longitudinal direction by the suture in the junction operation.

In the healing process after implantation, the outer periphery of the polytetrafluoroethylene tubing is first enveloped by the connective tissue and organizes, and afterwards the fibrin layer on the inner surface of the tubing organizes. At this time, there is established a continuity of the intimas of the host's vessels with the neointima of the inner surface of the vascular prosthesis, and simultaneously, the fibrin layer is replaced by the fibrous tissue which has entered the prosthesis through the fine pores from the periphery thereof. Furthermore, after a certain period of time, the neointimas at the inner surface are connected firmly to the connective tissue lining the outer wall of the prosthesis, thereby completing the formation of an artery. It is known that this artery formation requires a period of usually about 4 to 6 months. It is known on the other hand that with vascular prosthesis implanted in veins, the rate of entry of the connective tissue from the periphery thereof is slower than for arterial implantation.

Still another object of this invention is, therefore, to provide a vascular prosthesis of a stretched polytetrafluoroethylene tubing in which the pores on the outside surface are made larger than the pores on the inside surface thereby to increase the rate of entry of the connective tissue from the outer periphery. The smaller size of the pores of the inner surface is believed to reduce the surface stagnation of blood flow, with the result that platelet adhesion is reduced and the amount of thrombus formation at the inner surface decreases, as a result of which the fibrin layer is very thin and the thickness of the neointima on the inner surface is decreased when compared to the thickness of a similarly dimensioned prior art vascular prosthesis.

A further object of this invention is to provide a vascular prosthesis of a stretched polytetrafluoroethylene tubing in which the inside surface fibrous structure is finer than the outside surface fibrous structure, thereby allowing the connective tissue from the outer periphery to grow and develop fully, and consequently supplying enough nutrient to the neointima formed at the inner surface to prevent the calcification in the prosthesis wall that may otherwise occur due to degenerative change with the lapse of time, thus increasing the patency rate of the prosthesis after implantation.

The prosthesis in accordance with this invention has a micro-structure of fibers and nodes which are produced by stretching a tubing of polytetrafluoroethylene or a copolymer comprising tetrafluoroethylene and one or more other olefin monomers or a polymer blend of polytetrafluoroethylene and one or more other polyolefins of commercially available "fine powder" grades in at least one direction and then heating at least the outer surface of the stretched tubing while restraining it in the stretched state to a temperature of at least about 327° C. (the sintering temperature of PTFE) but preferably not above about 360° C. (sintering) while imposing a temperature gradient across the wall of the tubing.

In a preferred embodiment, the invention provides a tubular vascular prosthesis of a composite structure having a pore size of $1\mu$ to $5\mu$ at the inside surface and at least $3\mu$ at the outside surface and an average fiber diameter of $0.1\mu$ to $2\mu$ at the inside surface and an average fiber diameter at the outside surface of at least 2 times the value at the inside surface, and the entire prosthesis is defined by a porosity of 70% to 95% and a fiber length of not more than $40\mu$ by stretching (in the linear direction) at a stretch ratio of preferably about 100 to about 500% and expanding in the radial direction at a stretch ratio, followed by the above-described sintering step of about 20 to about 200%. Such a vascular prosthesis has enhanced junction tear strength in the implanting operation, and permits a thin neointima to form on the inner surface of the prosthesis after implantation. The inner cavity is not occluded, and the prosthesis has a high rate of patency. Porosity as described herein is determined by measuring the specific gravity by the method of ASTM D276-72 and the pore size distribution and bubble point as described herein are determined by the method of ASTM F316-70.

BRIEF DESCRIPTION OF THE ACCOMPANYING DRAWINGS

The objects and significance of the present invention will become apparent from the following detailed description taken in conjunction with the accompanying drawings in which.

DETAILED DESCRIPTION OF THE INVENTION

Figure 1:
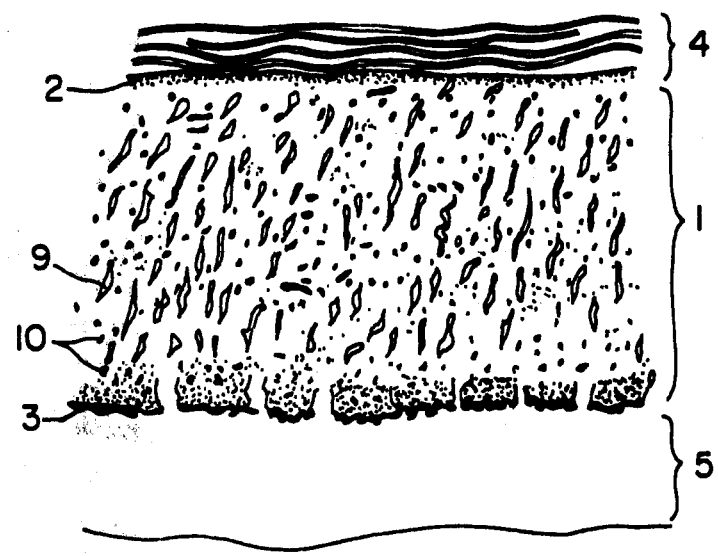
FIG. 1 is a schematic view of a vascular prosthesis that has been implanted.

Turning now to the figures, FIG. 1 schematically shows the wall of a prosthesis in cross section in order to describe the healing condition after a lapse of 8 to 10 months from the implantation of the prosthesis in a part of a femoral artery.

The wall 1 of the prosthesis has an inside surface 2 and an outside surface 3, and a neointima 4 uniformly covers the inside surface 2. On the other hand, a connective tissue 5 composed mainly of a collagen substance adheres firmly to the outside surface 3, and fibroblast growth and capillary formation are observed. The fibroblasts contain a spherical nucleus 10, and are uniformly distributed on the tubular wall 1 as black dots. The tubular wall of the prosthesis is a composite structure composed of irregularly-shaped nodes 9 and fine fibers (not shown) connecting the nodes together.

Figure 2:
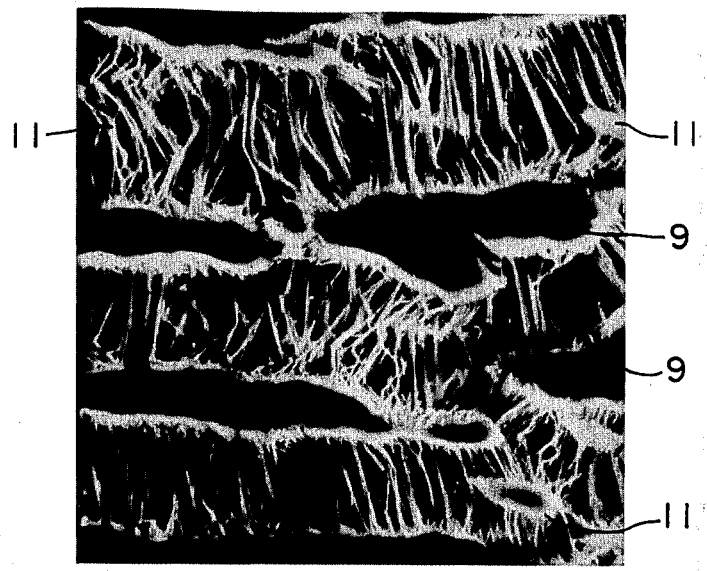
FIG. 2 is a scanning type electron microphotograph of the inner surface of a vascular prosthesis of polytetrafluoroethylene in accordance with this invention that has been stretched only in the linear direction.
Figure 3:
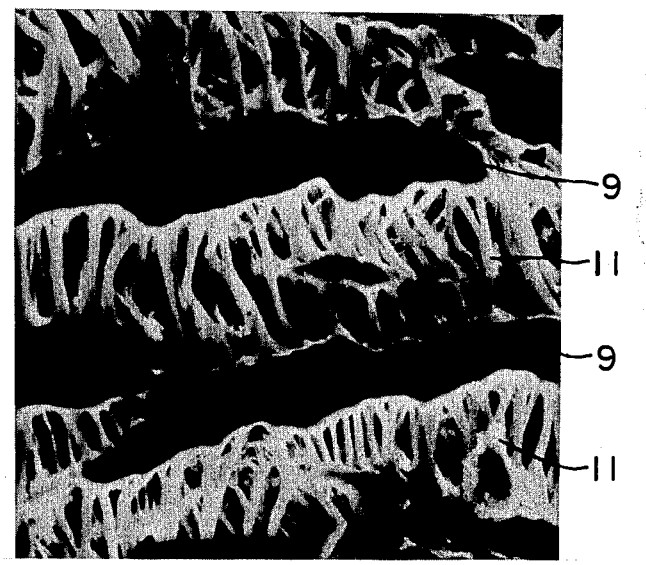
FIG. 3 is a scanning type electron microphotograph of the outer surface of the same vascular prosthesis.

FIGS. 2 and 3 are scanning type electron microphotographs (1,000×magnification) of the inside surface 2 and the outside surface 3 of a prosthesis in accordance with the invention that has been stretched linearly but not expanded radially. The nodes 9 composed of polytetrafluoroethylene are interconnected with a number of fibers 11 which are aligned substantially at right angles to the long-axis direction of the ellipsoidal nodes 9. The diameter of the fibers 11 at the inside surface 2 (FIG. 2) of the prosthesis of this invention is not more than ½ of the diameter of the fibers 11 at the outside surface 3 (FIG. 3), and in these photographs, the fibers have a diameter of 0.5 to $1.0\mu$ at the inside surface, and 1.0 to $3.0\mu$ at the outside surface.

Figure 4:
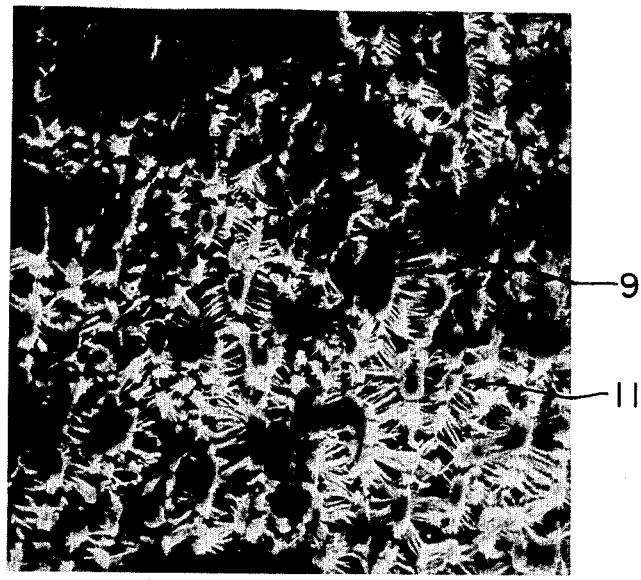
FIG. 4 is a scanning type electron microphotograph of the inner surface of a similar vascular prosthesis which has been both stretched linearly and expanded radially.

FIG. 4 is a scanning type electron microphotograph (magnification 400×) of the inside surface of a biaxially stretched (i.e., linearly and radially) tubing of polytetrafluoroethylene in accordance with the present invention. It can be seen from the microphotograph that nodes 9 and fibers 11 of the polytetrafluoroethylene are both reduced in dimension. The fibers 11 have a diameter of 0.1 to $0.6\mu$.

Figure 5:
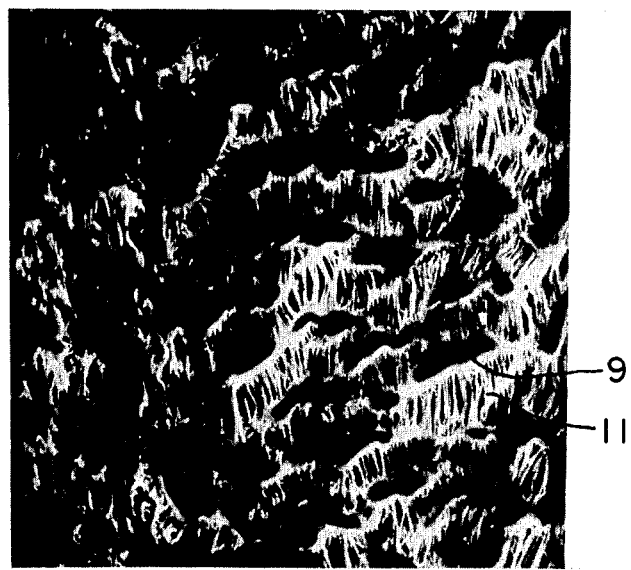
FIG. 5 is a scanning type electron microphotograph of the outside surface of the same vascular prosthesis as shown in FIG. 4.

FIG. 5 shows the outside surface of the same prosthesis as shown in FIG. 4.

Descriptions with regard to the diameter of each fiber and the average diameter of the fibers are given below. The diameters of the individual fibers under a microscope vary considerably according, for example, to the selection of visual field, and the manner of developing the photograph of a sample. The number of fibers appearing in one photograph in FIG. 2 or 3 is several hundred, and several fibers aligned in a slightly deviating manner in the planar direction are overlapping and look as if they are one thick fiber. For this reason, in order to determine the average fiber thickness, the diameters of at least 3,000 fibers must be measured on the basis of at least 10 photographs, and then an average value of the diameters calculated. At this time, experts in photographic examination can see relatively easily whether a number of fine fibers are aligned in parallel, or whether they form one coalesced thick fiber. In the case of an assembly of fine fibers, transmission (transparency) increases is the planar direction, and the thickness of the fibers is not perceived. However, a coalesced thick fiber can be clearly detected using scanning type electron microphotograph as a fiber having a thickness. Hence, in determining the average fiber diameter, fibers aligned in a planar direction and having a small thickness must be excluded from the calculation, and only the diameters of distinguishable fibers must be summed to arrive at the average.

In order to stretch and expand tubings of polytetrafluoroethylene, the methods described in Japanese Patent Publication No. 13560/67 and U.S. Pat. No. 3,953,566 can basically be utilized. For example, about 15 to 40 vol% of a liquid lubricant such as mineral oil, liquid paraffin, naphtha, etc., is mixed with a fine powder (e.g., a powder having a particle size of about 0.1 to about $0.5\mu$ and a surface area of about 5 to about 15 $m^2/g$) of polytetrafluoroethylene, and the mixture extruded into a tubular form using a ram-type extruder. Any type of polytetrafluoroethylene can be used in this invention and those having a molecular weight of about 2,000,000 to about 4,000,000 are preferred. The tubing is then stretched in at least one direction while it is heated at a temperature below the sintering temperature (i.e., about 327° C.). Then, while the tubing is fixed so that the tubing does not shrink, it is heated to a temperature of at least about 327° C. to set the stretched and expanded structure and thereby to form a tubing having increased strength. Without modifying this procedure, however, a tubing in which the fibrous structure differs between the inside surface and the outside surface cannot be obtained. In order to obtain the structure in accordance with this invention, the tubing should be heated from its outer periphery while being forcibly cooled at its inside surface to form a temperature gradient through the thickness of the tube wall increasing in temperature toward the outer periphery during the sintering process. For this purpose, the inner surface of the tubing is continuously exposed to air at a temperature ranging from room temperature (about 20° to 30° C.) to about 327° C. by continuously introducing such air into the inside cavity of the tubing either forcibly or by a continuous pressure reduction in the inside cavity of the tubing, in such manner that the outside surface of the tubing is heated to a temperature of at least 327° C. The inner surface may or may not be heated to the sintering temperature. However, the inner surface must always be at a lower temperature than the outer surface during the sintering process.

Expanding of the tubing in the radial direction thereof can optionally be performed continuously by reducing the pressure surrounding the tubing. This may be performed simultaneously with the length-wise or linear stretching, but is preferably performed separately, after linear stretching but before sintering.

Naturally, the number, length, diameter, etc., of fine fibers formed vary depending on the degrees of stretching and expansion in the longitudinal and radial directions, respectively, and can be appropriately selected depending on the desired porosity, pore size, softness, and tear strength. When the degrees of stretching and expanding are approximately equal, the fine fibers are uniformly distributed radially from spherical nodes, and despite this, the directions of fiber alignment differ between the inside surface and the outside surface of the tubing. If either of linear stretching or radial expanding is carried out to a substantially greater degree than the other, fine fibers in the direction of higher stretch or expansion are longer and larger in number. However, in a direction at right angles to that direction, the fibers are shorter and fewer in number.

It can be ascertained from electron-microscopic examination that the size of the nodes and the diameter of the fibers in a tubing subjected to stretching and expansion in two directions show greater changes than those of a tubing subjected to stretching or expansion in only one direction. It can be seen particularly that the fibers are distributed in a more radial direction at the inside surface than at the outside surface.

With increasing stretch ratio, the size of the nodes decreases progressively. When the tubing is stretched in one direction, the nodes have the form of elongated ellipsoids. But after treatment in two directions, the size of the nodes becomes $\frac{1}{8}$ to 1/10 of that after a stretching in one direction, and in many cases, the nodes assume a substantially spherical form.

The diameter of the fibers after stretching in one direction is almost constant at 0.5 to $1\mu$ regardless of the stretch ratio, but treatment in two directions causes the fibers to decrease in diameter to $\frac{1}{8}$ to 1/5, whereby the number of fibers increases correspondingly.

The temperatures used for stretching, expanding and sintering are described below.

Stretching or expanding causes the tubing to attain a dimension and a shape which are different at least from the dimension and shape before the treatment. At least an external force must be exerted in order to cause this change. Similar to thermoplastic resins, in general, this force tends to be lower at higher tube temperatures and higher at lower tube temperatures. This external force required for deformation is comparable to the strength which the tubing itself possesses as a result of being oriented in fibrous form by extrusion. The strength built up by the extrusion-forming depends greatly on the extruding conditions. When the temperature for deformation of the tubing by stretching or expanding is below a certain limit, the external force required for deformation is higher than the strength of the tubing, and breakage increases during deformation. On the other hand, when the temperature is above this certain limit, thhe external force for deformation becomes lower than the strength of the tubing, and breakage abruptly decreases. Accordingly, in the deformation of the tubing, there is a lower limit to the temperature depending on the extruding conditions.

The same tendency exists in the rate of deformation by stretching or expanding. When the rate of deformation increases, the external force required for deformation increases. Thus, in order to prevent a breakage of the tubing, it is necessary to heat the tubing at still higher temperatures.

The minimum temperature for deformation cannot be definitely set forth because the strength of the tubing varies depending on the tube extruding conditions. Those skilled in the art, however, can easily determine the minimum deformation temperature.

The sintering step comprises a heating, e.g., until completely melted, of a stretched uniaxially, or stretched/expanded biaxially tubing to a temperature of at least 327° C. while the tubing is fixed so that shrinkage does not occur. A difference in the porous fibrous structures of the inside and outside surfaces of the tubing can be achieved by heating the outside of the tubing while cooling the inside surface of the tubing by passing air through the cavity of the tubing. By increasing the amount of air passed through the cavity of the tubing or reducing the temperature of the air, it is possible to heat the outside surface of the tubing to a temperature of at least 327° C. while at the same time maintaining the inside surface of the tubing at a temperature below 327° C. In such a tubing, only the outside surface is sintered, and the inside surface remains unsintered. Thus, the shapes and sizes of the fibers and nodes differ greatly between the inside surface and the outside surface. Alternatively, the inside surface of the tubing can be heated to a temperature of above 327° C. by decreasing the amount of air passed through the cavity of the tubing or increasing the temperature of the air. This can also be accomplished by increasing the length of the heating zone or increasing the heating zone temperature. As a result, fibers at the outside surface of the tubing are exposed to a temperature of at least 327° C. for long periods of time, and, while initially they have the same structure (particularly, diameter) as those on the inside surface, they gradually become thicker as a result of coalescence. For example, four fibers are fused and coalesced together to form a single fiber having a diameter twice that of each single fiber before sintering.

The thickness of the inside surface sturcture becomes different from that of the outside surface structure by changing the amount of coooling air passed through the cavity of the tubing and the amount of heat supplied externally. Increasing the amount of external heat supplied results in an increase in the outside wall thickness of the thicker fibrous diameter or large pore size, and if the amount of cooling air is increased, the inside wall thickness of the thinner fibrous diameter or small pore size increases. In this case, however, the size of the nodes does not change, and therefore, the size of the nodes at the outside surface is substantially the same as that of the nodes at the inside surface.

As shown in FIG. 4, when a longitudinally stretched tubing is further expanded in its radial direction, the size of nodes 9 and the diameter of fibers 11 change drastically.

The nodes 9 in FIGS. 2 and 3 are ellipsoidal and have a relatively uniform size. But in the biaxially stretched and expanded tubing, nodes 9 formed as a result of uniaxial stretching are divided into smaller portions depending on the degree of expansion, and fibers 11 occur among the separated nodes. The fibers 11 in FIGS. 2 or 3 have a diameter of approximately $0.5\mu$ to $2\mu$, although the diameter varies somewhat depending on the conditions of tubing preparation. However, the fibers 11 after stretching and expanding biaxially as in FIG. 4 have a diameter of $0.1\mu$ to $0.5\mu$. As a result of expansion biaxially, the diameter of the fibers 11 between the nodes 9 becomes $\frac{1}{3}$ to 1/5 of that of the fibers of tubing that has been stretched only uniaxially. Consequently, a single fiber 11 that occurs after the uniaxial expansion is again divided into 10 to 30 fine fibers as a result of the second, radial expansion.

FIG. 4 shows the inside surface fibrous structure of the biaxially expanded tubing. Just as in the relation between FIGS. 2 and 3, the fibers at the outside surface attain a diameter at least two times larger than that of the fibers at the inside surface by sintering the tubing while forcibly cooling the inside surface.

The fiber alignment of the inside surface can be made drastically different from that of the outside surface by increasing both the amount of cooling air passed through the cavity of the tubing and the amount of heat supplied externally. An example is shown in FIG. 4 (inside surface) and FIG. 5 (outside surface).

The fibrous structure at the outside surface of the tubing is less dense than that at the inside surface, but each fiber is thicker and this produces various effects as described below.

Firstly, this serves to increase the mechanical strength of vascular prostheses made of such a tubing whereby preventing a suture from tearing the prosthesis in the longitudinal direction during implant surgery. It is possible for only the inner surface fibrous structure of the tubing to act as a bag-like receptacle for transporting blood. But for application to arteries, the tubing must withstand a blood pressure of about 120 mmHg, and should not be compressed by elastic fibroblasts that develop on the outer periphery thereof. In addition, the tubing must withstand suturing at the time of surgical operation. The force required to cut the fibers can be increased by increasing the diameters of the fibers at the outside surface of the tube, and increasing the number of fibers that are aligned at right angles to the direction of possible tearing. In particular, a tubing that has been biaxially stretched and then sintered to increase the fiber diameter has improved tear strength.

Secondly, as a result of decreasing the dimension of the fibrous structure at the inside surface of the vascular prosthesis made of the polytetrafluoroethylene tubing, its surface resistance to flow of blood is reduced, and consequently, platelet adhesion is reduced. Platelets which have contacted the surface of the prosthesis and adhered thereto aggregate reversibly with adenosine diphosphate and calcium ion, after which they become irreversibly adhered and form a thrombus together with fibrin. The thrombus layer becomes thinner as the amount of platelets that have adhered decreases. The thickness of the initial thrombus layer increases as the fibrin deposits onto it, and this finally causes occlusion.

In order, therefore, to obtain vascular prostheses free from occlusion, it is essential to decrease the thickness of the initial thrombus layer. This effect is more pronounced in veins than in arteries. In other words, a reduction in the thickness of neointimas on the inner surface of the prostheses can be expected.

As a third effect, fibroblasts rapidly enter the prosthesis from the outer periphery of the prosthesis and grow fully as a result of the increase in the size of the openings in the outer surface fibrous structure of the prosthesis. It is already known that fibroblasts readily enter a vascular prosthesis made of a knitted or woven fabric of Dacron, or polytetrafluoroethylene, etc., because such a proshthesis has a tubular wall of a loose structure. However, bleeding occurs through the wall immediately after implantation, and this results in an increase in the thickness of the fibrin layer on the inner surface of the prosthesis. Further increase leads to calcification and occlusion. In a prosthesis made of polytetrafluoroethylene having the same fibrous structures both at the outside surface and at the inside surface, it is essential to decrease the thickness of the fibrin layer that results from platelet adhesion by making the pore size sufficiently small to prevent bleeding, and therefore, the ease of entry of fibroblasts from the outer periphery of the prosthesis must be sacrificed somewhat.

When the fibrous structure differs between the outside surface and the inside surface of a prosthesis as defined by its fiber diameter, i.e., the spaces between fibers, or pores, at the outside surface being at least two times that at the inside surface, as in the present invention, the thickness of the fibrin layer at the inner surface can be decreased, and at the same time, entry of fibroblasts from the periphery can be facilitated. Furthermore, nutrient supply to the neointimas occurring at the inner surface of the prosthesis can be effected sufficiently through capillaries which densely develop on fully grown fibroblasts. Thus, it is possible to greatly reduce calcification of the neointimas that may result from nutritional deficiency.

In arterial prostheses, nutrition can be effected not only through capillaries at the fibroblasts, but also from the blood within the cavity of the prostheses. However, in venous prostheses, nutrition from the blood can hardly be expected, and reliance must be exclusively on the capillaries present on the fibroblasts that have come through the outer periphery for nutrient supply. Accordingly, the entry of fibroblasts from the outer periphery of vascular prostheses is important not only for the formation of neointimas, but also for preventing calcification of the neointimas which may be caused by a nutritional deficiency after implantation and thereby for increasing the patency rate of the prosthesis after operation. This is more important in venous prostheses.

The relation between the mean pore size and the length and diameter of fibers among the nodes in a microstructure consisting of very fine fibers of polytetrafluoroethylene and nodes connected to one another by the fibers is described below.

If the length of each fiber connecting nodes is $l$ and the distance between two fibers is $d$, then the sectional surface of a rectangle surrounded by the two fibers and the nodes has the following relation with regard to the fluid dynamical equivalent pore size $\gamma$.

$$2/\gamma = (1/l) + (1/d)$$

Since $l$ is usually far larger than $d$, $\gamma$ becomes approximately equal to $2d$. Ultimately, the structure can be described as a porous structure having a fluid dynamical equivalent pore size twice the interfiber distance. It is believed that the number of fibers occurring between two nodes is approximately the same for both the outside surface and inside surface of the tubing (before sintering). In order for fibers at the outer surface to attain a diameter at least two times larger than those at the inside surface as a result of sintering at 327° C. or higher while cooling the inside surface, at least four fibers must be coalesced to form one thick fiber. At this time, the distance $D$ between adjacent large diameter fibers becomes approximately four times the distance $d$ between fine fibers, and as a result, the fluid dynamical equivalent pore size becomes about fourfold. Since the distribution of fibers between nodes is not planar as in the above calculation but three-dimensional, the equivalent pore size of the outside surface does not become four times the equivalent pore size of the inside surface. However, the pore size is certainly at least two times that of the inside surface.

A certain relation exists between the porosity and fiber length of the wall of a prosthesis, and there is a tendency for the length of fiber to increase with increasing porosity. Vascular prostheses must have pore sizes which are small enough to keep the blood during circulation from leaking through the tubular wall, and are large enough to permit entry of fibroblasts from the outer periphery without obstruction. In order to meet this requirement, the porosity and the fiber length should be within certain specified ranges.

The length of fiber increases approximately proportionally to the ratio of stretch in the longitudinal direction, and the ratio of expansion in the radial direction, of a tubing formed by a ram extruder. Because the fibers occur when the structure forming the original tubular wall is progressively split into the nodes, both ends of the fibers join the nodes. Spaces surrounded by the nodes and the fibers become pores. The porosity of the tubing is low when the nodular size is large and the fiber length is small, and the porosity is high when the nodular size is small and the fiber length is large. When the tubing is stretched biaxially, the porosity of the tubing can be much increased than the porosity of a tubing which is stretched uniaxially and has the same fiber length.

If the porosity is too high, there is a possibility of blood leaking, and tearing of the tubular wall of the prosthesis by the suture during suturing operation can occur. Prostheses having a porosity of more than 96% are not practical, and those having a porosity of less than 60% have a short fiber length and prevent entry of fibroblasts after implantation. The most preferred porosity is within the range of 70% to 95%. It has been clinically confirmed that the preferred range somewhat differs between arterial prostheses and venous prostheses.

As described hereinabove, the fiber length is proportional to the porosity, and prostheses defined by a fiber length of less than about 40μ are preferred in this invention.

Another significant factor for growing neointimas on the inside surface of prostheses and preventing them from degeneratively changing with time is the thickness of the tubular wall of the prostheses. With prostheses comprising a fibrous structure only at the inside surface, there is a certain limit to the distance through which fibroblasts enter the prostheses from the outside surface. Consequently, the distance over which nutrient is supplied is also limited. It has been found clinically that the maximum thickness of the tubular wall is about 0.8 mm. In the present invention, the wall thickness of the fibrous structure at the inside surface and that of the fibrous structure at the outside surface can be varied depending on the conditions of preparation of the tubing. For example, by adjusting the thickness of the inside surface layer to 0.4 mm and the outside surface layer to 0.4 mm, the distance of fibroblast entry can be adjusted substantially to 0.4 mm.

The prostheses defined by the properties described hereinabove serve to facilitate the suturing technique in operation and expedite the healing of patients after operation. Since neointimas are maintained free from degenerative change with their use, occlusion does not occur. Accordingly, the prostheses in accordance with this invention contribute greatly to not only to surgery but also to industry.

The following example is given to illustrate the invention in greater detail.

EXAMPLE 2 kg of a commercially available polytetrafluoroethylene (TEFLON 6, a trademark for a product of E.I. du Pont de Nemours & Co.) and 0.52 kg of a white oil (Sumoil P-55, a trademark for a product of Muramatsu Sekiyu Kabushiki Kaisha) were mixed, and the mixture was formed into a tubing having an inside diameter of 4 mm and an outside diameter of 6 mm using a ram-type extruder. The tubing was then heated to a temperature below the boiling point of the white oil (i.e., 180°–250° C.) to remove the white oil. The tubing (20 cm long) was rapidly stretched to a length of 100 cm while heating the tubing at 200° C. The stretched tubing was fixed at both ends to prevent shrinkage. At the same time, a pipe for introducing a cooling air was connected to one end of the tubing, and the other end was sealed. The tubing was placed in a furnace, and the temperature of the furnace was gradually increased. When the temperature reached 320° C., air (at 200° C.) at a pressure of 0.4 kg/cm² was abruptly introduced, and while maintaining the air at this pressure and at the temperature of 200° C., the temperature of the furnace was increased at 440° C. at the highest. After confirming the temperature was 440° C., the tubing was rapidly cooled to room temperature (about 20° to 30° C.).

The inside and outside surfaces of the resulting tubing were photographed using a scanning type electron microscope (1,000×), and the mircophotographs obtained are shown in FIGS. 2 and 3. It was determined that the fiber diameter was 0.5 to 1.0μ at the inside surface and 1.0 to 3.0μ at the outside surface. The fiber length was 15 to 30μ both at the inside and outside surfaces. The tubing as a whole had a porosity of 81%.

For comparison, a tubing was produced under the same conditions as set forth above except that air was not introduced into the inside cavity of the tubing. The resulting tubing showed a similar structure to FIG. 2 at the inside and outside surfaces, but the porosity had descreased to 76%. The pore size of the tubing in this comparison was measured, and it was found that its bubbling point determined using isopropyl alcohol (according to ASTM F316-70) was 0.15 kg/cm², and its mean pore size (according to ASTM F316-70) was 2.5μ. Hence, the comparison tubing was believed to have much the same pore size as the inside surface of the tubing shown in FIG. 2.

It was impossible on the other hand to directly measure the pore size of the outside surface in FIG. 3. From the fiber diameter and the interfiber distance determined from FIG. 3, the mean pore size of the outside surface was considered to be about four times (i.e., about 7μ) that of the inside surface.

The tubing stretched to five times at 200° C. as set forth above was connected to a pipe for supplying cooling air. When the temperature of the furnace became 325° C., air at a pressure of 0.9 kg/cm² was introduced. The tubing was thus expanded to an outside diameter of 8 mm. After increasing the temperature of the furnace to 480° C. at the highest, the tubing was rapidly cooled. The fiber diameter of the resulting tubing was 0.4 to 0.8μ at the inside surface and 1 to 3μ at the outside surface, and the tubing as a whole had a porosity of 89%.

Air at a pressure of 1.5 kg/cm² was introduced into the tubing stretched five times at 200° C. as set forth above when the furnace temperature reached 330° C. This resulted in the expansion of the outside diameter of the tubing to 16 mm. The air pressure was reduced to 0.4 kg/cm², and the furnace temperature was increased to 465° C. at the highest, after which the tubing was rapidly cooled. The inside surfce of the resulting tubing was as shown in FIG. 4. The fiber diameter of the inside surface was 0.1 to 0.2μ, and the tubing as a whole had a porosity of 93%.

While the invention has been described in detail and with reference to specific embodiments thereof, it will be apparent to one skilled in the art that various changes and modifications can be made therein without departing from the spirit and scope thereof.

What is claimed is:

1. A vascular prosthesis comprising a tubing of porous polytetrafluoroethylene, said polytetrafluoroethylene tubing having a fibrous structure of nodes and fibers connecting the nodes together and having a structure in which the fibrous structure at the inside surface of the tubing is finer than the fibrous structure at the outside surface of the tubing.

2. The vascular prosthesis of claim 1, wherein said polytetrafluoroethylene tubing has a porosity of 70% to 95% and a fiber length of not more than 40μ.

3. The vascular prosthesis of claim 1, wherein the fibers have an average diameter of 0.1 to 2μ at the inside surface and at least twice the average diameter of the inside surface at the outside surface.

4. The vascular prosthesis of claim 2, wherein the fibers have an average diameter of 0.1 to 2μ at the inside surface and at least twice the average diameter of the inside surface at the outside surface.

5. The vascular prosthesis of claim 1, wherein the fibers at the inside surface are distributed more radially than the fibers at the outside surface.

6. The vascular prosthesis of claim 2, wherein the fibers at the inside surface are distributed more radially than the fibers at the outside surface.

7. The vascular prosthesis of claim 1, wherein the length of the long axis of each node at the outside surface is at least twice that of the long axis of each node at the inside surface.

8. The vascular prosthesis of claim 2, wherein the length of the long axis of each node at the outside surface is at least twice that of the long axis of each node at the inside surface.

9. The vascular prosthesis of claim 1, wherein the pores on the outside surface are made larger than the pores on the inside surface.

10. The vascular prosthesis of claim 2, wherein the pores on the outside surface are made larger than the pores on the inside surface.

11. A process for producing a vascular prosthesis of a fibrous structure, which comprises extruding unsintered polytetrafluoroethylene containing a liquid lubricant into a tubing, stretching the tubing at least in the longitudinal direction of the tubing, fixing the tube to prevent shrinkage thereof during heating and then heating the stretched tubing so that the temperature of the outside surface of the tubing is at least 327° C., and the temperature of the inside surface of the tubing is lower than that of the outside surface.

12. A process for producing a vascular prosthesis of a fibrous structure, which comprises extruding unsintered polytetrafluoroethylene containing a liquid lubricant into a tubing, stretching the tubing at least in the longitudinal direction of the tubing, fixing the tubing to prevent longitudinal shrinking during heating and then radially expanding the stretched tubing while heating the same tubing so that the temperature of the outside surface of the tubing is at least 327° C., and the temperature of the inside surface of the tubing is lower than that of the outside surface.

13. The process of claim 12, wherein the inside surface is not heated to a temperature of 327° C. or higher 14. The process of claim 11, wherein the pressure outside the tubing is reduced when the tubing is heated.

15. The process of claim 12, wherein the pressure outside the tubing is reduced when the tubing is heated.

16. The process of claim 13, wherein the pressure outside the tubing is reduced when the tubing is heated.

17. The process of claim 11, wherein the tubing is heated from the outside surface of the tubing and cooling air is passed through the cavity of the tubing.

18. The process of claim 12, wherein the tubing is heated from the outside surface of the tubing and cooling air is passed through the cavity of the tubing.

19. The process of claim 13, wherein the tubing is heated from the outside surface of the tubing and cooling air is passed through the cavity of the tubing.

* * * * *